United States Patent [19]

Rieker

[11] Patent Number: 5,276,157
[45] Date of Patent: Jan. 4, 1994

[54] PROCESS FOR THE PURIFICATION OF 2,3-PYRIDINE AND QUINOLINEDICARBOXYLIC ACID DIESTER COMPOUNDS

[75] Inventor: William F. Rieker, Clark, N.J.

[73] Assignee: American Cyanamid Company, Wayne, N.J.

[21] Appl. No.: 812,517

[22] Filed: Dec. 20, 1991

[51] Int. Cl.$^5$ .......................................... C07D 213/803
[52] U.S. Cl. ...................................... 546/321; 546/168
[58] Field of Search ........................ 546/250, 168, 321

[56] References Cited

U.S. PATENT DOCUMENTS

| 4,460,776 | 9/1992 | Wepplo | 546/250 |
| 4,723,011 | 2/1988 | Doehner | 546/250 |
| 4,904,816 | 2/1990 | Cevasco et al. | 560/44 |
| 4,997,947 | 3/1991 | Szczepanski | 546/278 |

FOREIGN PATENT DOCUMENTS

| 0292032 | 11/1988 | European Pat. Off. | 546/278 |
| 0299362 | 1/1989 | European Pat. Off. | 546/278 |

OTHER PUBLICATIONS

Konishi, Chemical Abstracts, 86:139407g May 5, 1977.
Sumi et al., Chemical Abstracts, 70:67660d Sep. 25, 1967.

Primary Examiner—C. Warren Ivy
Assistant Examiner—Zinna N. Davis
Attorney, Agent, or Firm—John W. Hogan, Jr.

[57] ABSTRACT

The present invention provides a process for the purification of 2,3-pyridine and quinolinedicarboxylic acid diester compounds via extraction with a mineral acid.

20 Claims, No Drawings

PROCESS FOR THE PURIFICATION OF 2,3-PYRIDINE AND QUINOLINEDICARBOXYLIC ACID DIESTER COMPOUNDS

BACKGROUND OF THE INVENTION

The discovery, development and commercialization of the 2-(2-imidazolin-2-yl)pyridine and quinoline compounds as herbicidal agents has given new meaning to the term "weed control"; for within this series of compounds it has been found that some are broad-spectrum or total vegetation herbicides with activity in both herbaceous and woody plants. Others are highly selective weed control agents useful as weed control agents in the presence of crops.

Several processes for the preparation of the herbicidal 2-(2-imidazolin-2-yl)pyridines involve the preparation of 2,3-pyridinedicarboxylic acids from 2,3-pyridinedicarboxylic acid diesters, but methods for the preparation of 2,3-pyridinedicarboxylic acid diesters produce impure products. Current methods of production of 2.3-pyridinedicarboxylic acid diesters by various condensation routes provide very impure products (20% to 50% purity). Arduous or time-consuming purification methods are required to provide purified 2.3-pyridinedicarboxylic acid diesters. Distillation has been used to improve the purity initially to as high as about 65% to 70%. However, the distillation is done at high temperatures and at high vacuum and the distillation product is further purified by a second distillation to obtain purified 2,3-pyridinedicarboxylic acid diesters.

Since the purity of the 2,3-pyridinedicarboxylic acid diesters impact directly on the purity of the 2,3-pyridinedicarboxylic acids, a process that would improve the purity of the 2.3-pyridinedicarboxylic acid diesters without requiring the use of time-consuming distillation procedures would provide a great improvement in the processes used to prepare the herbicidal 2-(2-imidazolin-2-yl)pyridine and quinoline compounds.

It is an object of the present invention to provide a process for the purification of 2,3-pyridine and quinolinedicarboxylic acid diester compounds which avoids the use of the arduous or time-consuming purification methods of the prior art.

SUMMARY OF THE INVENTION

The present invention relates to an efficient process for the purification of 2,3-pyridine and quinolinedicarboxylic acid diesters of formula I

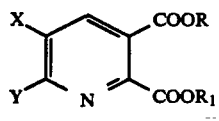

wherein
X and Y are each independently hydrogen, halogen, $C_1-C_6$ alkyl, $C_1-C_4$ hydroxyalkyl, $C_1-C_4$ alkoxyalkyl, $C_1-C_6$ alkoxy, $C_1-C_4$ alkylthio, phenoxy, $C_1-C_4$ haloalkyl, nitro, cyano, $C_1-C_4$ alkylamino, di-loweralkylamino $C_1-C_4$ alkylfulfonyl or phenyl optionally substituted with a $C_1-C_4$ alkyl, $C_1-C_4$ alkoxy or halogen group; and, when taken together, X and Y may form a ring in which XY is represented by the structure

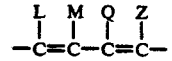

wherein L, M, Q and Z are each hydrogen, halogen, $C_1-C_4$ alkyl or $C_1-C_4$ alkoxy; and
R and $R_1$ are each independently
$C_1-C_6$ alkyl optionally substituted with $C_1-C_4$ alkoxy or phenyl optionally substituted with one to three $C_1-C_4$ alkyl groups, $C_1-C_4$ alkoxy groups or halogen atoms, or
phenyl optionally substituted with one to three $C_1-C_4$ alkyl groups, $C_1-C_4$ alkoxy groups, or halogen atoms;
which comprises extracting an impure mixture containing the said formula I compound, optionally in the presence of a solvent, with at least about 2.0 molar equivalents of a 40% to 85%. by weight, mineral acid solution. The aqueous acid extract is neutralized with base to provide purified formula I compounds directly or by extracting the neutralized mixture with a solvent. Alternatively, the aqueous acid extract is diluted with water and extracted with a solvent to provide purified formula I compounds.

Advantageously, the process of the invention avoids the use of time-consuming distillation purification procedures. Furthermore, the mineral acid present in the aqueous acid solution, after extraction with a solvent, is readily recycled into the process of the invention.

DETAILED DESCRIPTION OF THE INVENTION

In one of the preferred embodiments of the invention, the formula I pyridine and quinolinedicarboxylic acid diester compounds are purified by washing a mixture of an impure formula I compound and a solvent with between about 0.2 to 1.2 molar equivalents of a 5% to 20%, by weight, mineral acid solution, extracting the washed organic mixture with at least about 2.0 molar equivalents, preferably about 2.0 to 6.0 molar equivalents, of a 40% to 85%, by weight, mineral acid solution, diluting the concentration of the mineral acid in the aqueous acid extract to a value of about 5% to 30%, by weight, with water and extracting the diluted aqueous acid extract with a solvent to obtain purified formula I compounds.

Advantageously, the dilute acid wash removes acid soluble impurities from the impure formula I compound. Since the acid soluble impurities are removed, a purer formula I compound is obtained from the aqueous mineral acid extraction.

Another embodiment of the invention comprises extracting an impure formula I compound, optionally in the presence of a solvent, with at least about 2.0 molar equivalents, preferably about 2.0 to 6.0 molar equivalents, of a 40% to 85%, by weight, mineral acid solution, diluting the concentration of the mineral acid in the aqueous acid extract to a value of 5% to 30%, by weight, with water and extracting the diluted aqueous acid extract with a solvent to obtain purified formula I compounds.

A further embodiment of the invention comprises extracting an impure formula I compound, optionally in the presence of a solvent, with at least about 2.0 molar equivalents, preferably about 2.0 to 6.0 molar equivalents, of a 40% to 85%, by weight, mineral acid solution, neutralizing the aqueous acid extract with base and extracting the neutralized aqueous extract with a solvent to obtain purified formula I compounds.

In the above embodiments of the invention, the purified formula I compounds may be isolated by evaporating the resultant extract, or the extract containing the purified formula I compound may be sent directly to the reaction used to obtain the corresponding pyridine or quinolinedicarboxylic acid compound.

mineral acids which are suitable for use in the present invention include sulfuric acid, hydrochloric acid, hydrobromic acid, phosphoric acid and the like with sulfuric acid being preferred. A 45% to 65%, by weight, mineral acid solution is preferred. Solvents which are useful in the present invention include aromatic hydrocarbons such as toluene, benzene and xylenes, halogenated aromatic hydrocarbons such as chlorobenzene and dichlorobanzenes, and the like. Toluene and chlorobenzone are preferred solvents. Bases suitable for use in the process of the invention include ammonium hydroxide, sodium carbonate, sodium bicarbonate and the like with Ammonium hydroxide being preferred.

The above processes are especially efficacious for the purification of formula I compounds wherein X and Y are each independently hydrogen, $C_1-C_6$ alkyl or $C_1-C_4$ alkoxyalkyl; and, when taken together, X and Y may form a ring in which XY is represented by the structure —CH=CH—CH=CH—; and R and $R_1$ are each independently $C_1-C_6$ alkyl.

Preferred formula I compounds that are purified by the processes of the invention are diethyl 5-ethyl-2,3-pyridinedicarboxylate, diethyl 2,3-pyridinedicarboxylate, diethyl 5-methoxymethyl-2,3-pyridinedicarboxylate, diethyl 2,3-quinolinedicarboxylate and diethyl 5-methyl-2,3-pyridinedicarboxylate.

The processes of the invention provide purified formula I compounds without requiring the use of arduous or time consuming distillations done at high temperatures and high vacuum.

Formula I compounds are described in U.S. Pat. No. 4,723,011; U.S. Pat. No. 4,997,947; European application 292-0931-A published Nov. 23, 1988 and European application 299-362-A published Jan. 18, 1989.

The purified formula I compounds are useful as starting materials for the preparation of herbicidal 2-(2-imidazolin-2-yl)pyridine and quinoline compounds having the structural formula II

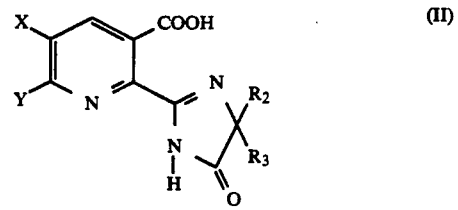

wherein $R_2$ is $C_1-C_4$ alkyl $R_3$ is $C_1-C_4$ alkyl or $C_3-c_6$ cycloalkyl; and when $R_2$ and $R_3$ are taken together with the carbon to which they are attached they may represent $C_3-C_6$ cycloalkyl optionally substituted with methyl; and X and Y are each independently hydrogen, halogen, $C_1-C_6$ alkyl, $C_1-C_4$ hydroxyalkyl, $C_1-C_4$ alkoxyalkyl, $C_1-C_6$ alkoxy, $C_1-C_4$ alkylthio, phenoxy, $C_1-C_4$ haloalkyl, nitro, cyano, $C_1-C_4$ alkylamino, diloweralkylamino, $C_1-C_4$ alkylsulfonyl or phenyl optionally substituted with a $C_1-C_4$ alkyl, $C_1-C_4$ alkoxy or halogen group; and, when taken together, X and Y may form a ring in which XY is represented by the structure

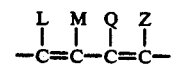

wherein L, M, Q and Z are each hydrogen, halogen, $C_1-C_4$ alkyl or $C_1-C_4$ alkoxy; and R and $R_1$ are each independently $C_1-C_6$ alkyl optionally substituted with $C_1-C_4$ alkoxy or phenyl optionally substituted with one to three $C_1-C_4$ alkyl groups, $C_1-C_4$ alkoxy groups or halogen atoms, or phenyl optionally substituted with one to three $C_1-C_4$ alkyl groups, $C_1-C_4$ alkoxy groups, or halogen atoms.

A method used to manufacture formula II 2-(2-imidazolin-2-yl)pyridine and quinoline herbicidal agents from formula I pyridine and quinolinedicarboxylic acid diesters is shown below in Flow Diagram I.

FLOW DIAGRAM I

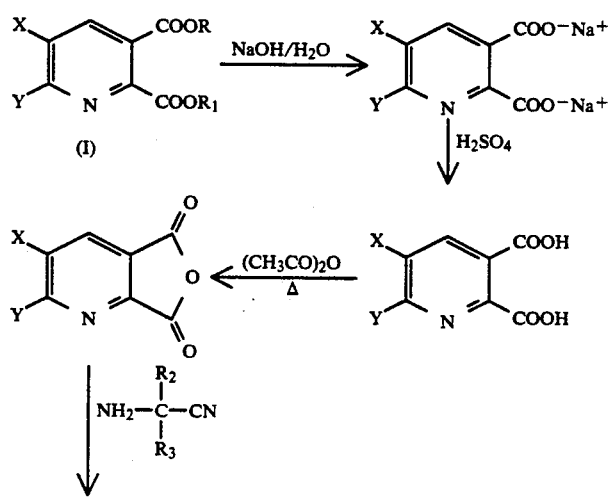

FLOW DIAGRAM I

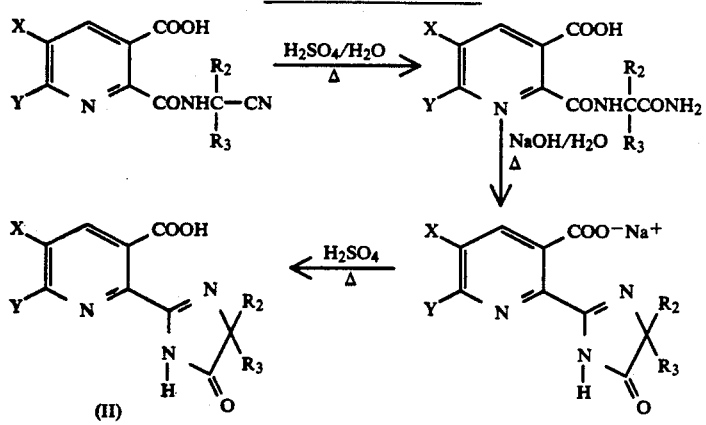

In order to facilitate a further understanding of the invention, the following examples are presented to illustrate more specific details thereof. The invention is not to be limited thereby except as defined in the claims. The term HPLC designates high pressure liquid chromatography.

EXAMPLE 1

Purification of Diethyl 5-ethyl-2,3-pyridinedicarboxylate with an initial dilute acid wash A 15%, by weight, sulfuric acid solution (0.200 mol) is added with stirring to a solution of diethyl 5-ethyl-2,3-pyridinedicarboxylate (100.00 g, 50.3% real, 0.200 mol) in toluene (400 ml). The organic layer is separated and extracted with 60%, by weight, sulfuric acid solution (0.651 mol). The aqueous extract is diluted with ice-water (316.50 g) and extracted with toluene (200 ml). The organic extract (228.4 g) is concentrated in vacuo to give purified diethyl 5-ethyl-2,3-pyridinedicarboxylate (55.26 g, 77.2% real, isolated yield 84.8%).

This example shows that when the impure diethyl 5-ethyl-2,3-pyridinedicarboxylate mixture is first washed with dilute sulfuric acid, to remove acid soluble impurities, followed by extraction with a strong sulfuric acid solution, that the purity of the said dicarboxylate is increased by 53.5% with an isolated yield of 84.8%.

EXAMPLES 2-10

Purification of Diethyl 5-ethyl-2,3-pyridinedicarboxylate by extraction with sulfuric acid A solution of diethyl 5-ethyl-2,3-pyridinedicarboxylate (34.46 g, 72.6% real, 0.10 mol) in toluene (65.54 g) is extracted with a 32.36%, by weight, sulfuric acid solution (0.2 mol). The organic phase is washed with 10% sodium bicarbonate solution and water. The combined water and sodium bicarbonate washes are washed with toluene and the toluene wash is combined with the organic phase. The organic phase is concentrated in vacuo to a constant weight and the unextracted diethyl 5-ethyl-2,3-pyridinedicarboxylate is then assayed by HPLC. The results of this example are summarized in Table I below.

Following the above procedure, but varying the sulfuric acid concentrations and number of equivalents utilized, gives the results summarize4 in Table I below.

TABLE I

Purification of Diethyl 5-ethyl-2,3-pyridinedicarboxylate

| | Example Number | | | | | | | | |
|---|---|---|---|---|---|---|---|---|---|
| | 2 | 3 | 4 | 5 | 6 | 7 | 8 | 9 | 10 |
| $H_2SO_4$ concentration (% w/w) | 32.36 | 43.06 | 64.35 | 48.40 | 59.45 | 77.05 | 57.98 | 68.10 | 82.48 |
| $H_2SO_4$ equivalents | 2 | 2 | 2 | 4 | 4 | 4 | 6 | 6 | 6 |
| Weight of unextracted diethyl 5-ethyl-2,3-pyridinedicarboxylate (g) | 20.3 | 13.13 | 3.41 | 2.85 | 0.52 | 0.20 | 0.21 | 0.33 | 0.37 |
| Purity of unextracted diethyl 5-ethyl-2,3-pyridinedicarboxylate (% w/w) | 73.6 | 65.9 | 37.5 | 34.6 | 10.5 | 5.1 | 4.8 | 8.3 | 3.6 |
| Calculated weight of extracted diethyl 5-ethyl-2,3-pyridinedicarboxylate (g) | 4.68 | 11.88 | 21.59 | 22.15 | 24.48 | 24.80 | 24.79 | 24.68 | 24.64 |
| Calculated purity of extracted diethyl 5-ethyl-2,3-pyridinedicarboxylate (% w/w) | 68.3 | 81.6 | 85.1 | 84.5 | 82.9 | 81.2 | 82.4 | 80.7 | 77.5 |
| Calculated extracted recovery of 5-ethyl-2,3-pyridinedicar- | 18.72 | 47.52 | 86.36 | 88.60 | 97.92 | 99.20 | 99.16 | 98.72 | 98.56 |

TABLE I-continued
Purification of Diethyl 5-ethyl-2,3-pyridinedicarboxylate

| | Example Number | | | | | | | | |
|---|---|---|---|---|---|---|---|---|---|
| | 2 | 3 | 4 | 5 | 6 | 7 | 8 | 9 | 10 |
| boxylate (%) | | | | | | | | | |

As can be seen from the data in Table I above, the purity of the diethyl 5-ethyl-2,3-pyridinedicarboxylate is generally improved to greater than 81% (up from 72.6%) using 2-6 equivalents of sulfuric acid solutions having concentrations greater than 43%. Although upon first inspection the increase in purity from 72.6% to generally greater than 81% may not appear to be a significant increase, it results in a dramatic improvement when commercially manufacturing the 2-(2-imidazolin-2-yl)pyridine and quinoline herbicides. Note that by employing the preferred 45%–65%, by weight, mineral acid solutions the purity of the diethyl 5-ethyl-2,3-pyridine dicarboxylate is improved to 82% to 85%.

EXAMPLE 11

Purification of neat Diethyl 5-ethyl-2,3-pyridinedicarboxylate by extraction with sulfuric acid Diethyl 5-ethyl-2,3-pyridinedicarboxylate (29.0 g, 70.2% real, 0.081 mol) is added to a stirred mixture of water (50 ml) and 96% sulfuric acid (30.37 g). The mixture is allowed to settle and the phases are separated. The aqueous layer, which contains a small amount of an oil, is stirred with diatomaceous earth (2.0 g), filtered and washed with water (10 ml). The combined filtrate and wash is neutralized with 30% Ammonium hydroxide solution (36.22 g) and extracted with toluene. The combined organic extracts are concentrated in vacuo to obtain a brown oil and a small amount of a solid. The oil is decanted from the solid to give purified diethyl 5-ethyl-2,3-pyridinedicarboxylate (19.78 g, 81.5% real, 79.2% real recovery).

I claim:

1. A process for the purification of a 2,3-pyridine or quinolinedicarboxylic acid diester having the structural formula I

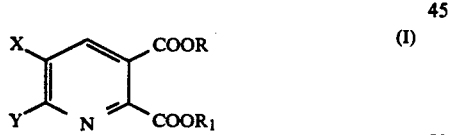

wherein

X and Y are each independently hydrogen, halogen, $C_1$–$C_6$ alkyl, $C_1$–$C_4$ hydroxyalkyl, $C_1$–$C_4$ alkoxyalkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino, $C_1$–$C_4$ alkylsulfonyl or phenyl optionally substituted with a $C_1$–$C_4$ alkyl, $C_1$–$C_4$ alkoxy or halogen group; and, when taken together, X and Y may form a ring in which XY is represented by the structure

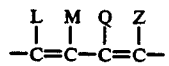

wherein L, M, Q and Z are each hydrogen, halogen, $C_1$–$C_4$ alkyl or $C_1$–$C_4$ alkoxy; and R and $R_1$ are each independently $C_1$–$C_6$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or phenyl optionally substituted with one to three $C_1$–$C_4$ alkyl groups, $C_1$–$C_4$ alkoxy groups or halogen atoms;

which comprises washing a mixture of an impure formula I compound and a first solvent with between about 0.2 to 1.2 molar equivalents of a 5% to 20%, by weight, mineral acid solution, extracting the washed organic mixture with at least about 2.0 molar equivalents of a 40% to 85%, by weight, mineral acid solution, diluting the concentration of the mineral acid in the aqueous acid extract to a value of 5% to 30%, by weight, with water and extracting the diluted aqueous acid extract with a second solvent to obtain a purified formula I compound.

2. The process according to claim 1 wherein the washed organic mixture is extracted with about 2.0 to 6.0 molar equivalents of a 45% to 65%, by weight, mineral acid solution.

3. The process according to claim 1 wherein the mineral acid is selected from the group consisting of sulfuric acid, hydrochloric acid, hydrobromic acid and phosphoric acid and the first solvent and second solvent are independently selected from the group consisting of toluene, benzene, a xylene, chlorobenzene and a dichlorobenzene.

4. The process according to claim 3 wherein the mineral acid is sulfuric acid and the first solvent and the second solvent are toluene.

5. The process according to claim 1 wherein X and Y are each independently hydrogen, $C_1$–$C_6$ alkyl or $C_1$–$C_4$ alkoxyalkyl; and, when taken together, X and Y may form a ring in which XY is represented by the structure —CH=CH—CH=CH—; and R and $R_1$ are each independently $C_1$–$C_6$ alkyl.

6. The process according to claim 5 wherein the 2,3-pyridine or quinolinedicarboxylic acid diester is selected from the group consisting of diethyl 5-ethyl-2,3-pyridinedicarboxylate, diethyl 2,3-pyridinedicarboxylate, diethyl 5-methoxymethyl-2,3-pyridinedicarboxylate, diethyl 2,3-quinolinedicarboxylate and diethyl 5-methyl-2,3-pyridinedicarboxylate.

7. The process according to claim 6 wherein the 2,3-pyridine or quinolinedicarboxylic acid diester is diethyl 5-ethyl-2,3-pyridinedicarboxylate.

8. A process for the purification of a 2,3-pyridine or quinolinedicarboxylic acid diester having the structural formula I

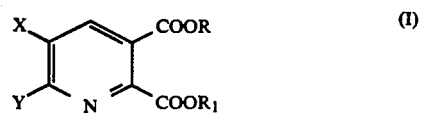

wherein

X and Y are each independently hydrogen, halogen, $C_1$–$C_6$ alkyl, $C_1$–$C_4$ hydroxyalkyl, $C_1$–$C_4$ alkoxyalkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino, $C_1$–$C_4$ alkylsulfonyl or phenyl optionally substituted with a $C_1$–$C_4$ alkyl, $C_1$–$C_4$ alkoxy or halogen group; and, when taken together, X and Y may form a ring in which XY is represented by the structure

wherein L, M, Q and z are each hydrogen, halogen, $C_1$–$C_4$ alkyl or $C_1$–$C_4$ alkoxy and R and $R_1$ are each independently
$C_1$–$C_6$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or phenyl optionally substituted with one to three $C_1$–$C_4$ alkyl groups, $C_1$–$C_4$ alkoxy groups or halogen atoms;

which comprises extracting an impure formula I compound, optionally in the presence of a first solvent, with at least about 2.0 molar equivalents of a 40% to 85%, by weight, mineral acid solution, diluting the concentration of the mineral acid in the aqueous acid extract to a value of 5% to 30%, by weight, with water and extracting the diluted aqueous acid extract with a second solvent to obtain a purified formula I compound.

9. The process according to claim a wherein the impure formula I compound is extracted with a mineral acid in the presence of a first solvent.

10. The process according to claim 8 wherein the mixture of an impure formula I compound is extracted with about 2.0 to 6.0 molar equivalents of a 45% to 65%, by weight, mineral acid solution.

11. The process according to claim a wherein the mineral acid is selected from the group consisting of sulfuric acid, hydrochloric acid, hydrobromic acid and phosphoric acid and the second solvent is selected from the group consisting of toluene, benzene, a xylene, chlorobenzene and a dichlorobenzene.

12. The process according to claim 11 wherein the mineral acid is sulfuric acid and the first solvent is toluene.

13. The process according to claim 8 wherein the 2,3-pyridine or quinolinedicarboxylic acid diester is selected from the group consisting of diethyl 5-ethyl-2,3-pyridinedicarboxylate, diethyl 2,3-pyridinedicarboxylate, diethyl 5-methoxymethyl-2,3-pyridinedicarboxylate, diethyl 2,3-quinolinedicarboxylate and diethyl 5-methyl-2,3-pyridinedicarboxylate.

14. A process for the purification of a 2,3-pyridine or quinolinedicarboxylic acid diester having the structural formula I

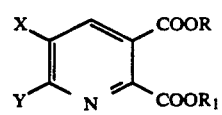

wherein
X and Y are each independently hydrogen, halogen, $C_1$–$C_6$ alkyl, $C_1$–$C_4$ hydroxyalkyl, $C_1$–$C_4$ alkoxyalkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino, $C_1$–$C_4$ alkylsulfonyl or phenyl optionally substituted with a $C_1$–$C_4$ alkyl, $C_1$–$C_4$ alkoxy or halogen group; and, when taken together, X and Y may form a ring in which XY is represented by the structure

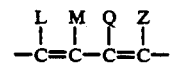

wherein L, M, Q and Z are each hydrogen, halogen, $C_1$–$C_4$ alkyl or $C_1$–$C_4$ alkoxy and R and $R_1$ are each independently
$C_1$–$C_6$ alkyl optionally substituted with $C_1$–$C_4$ alkoxy or phenyl optionally substituted with one to three $C_1$–$C_4$ alkyl groups, $C_1$–$C_4$ alkoxy groups or halogen atoms, or phenyl optionally substituted with one to three $C_1$–$C_4$ alkyl groups, $C_1$–$C_4$ alkoxy groups or halogen atoms;

which comprises extracting an impure formula I compound, optionally in the presence of a first solvent, with at least about 2.0 molar equivalents of a 40% to 85%, by weight, mineral acid solution, neutralizing the aqueous acid extract with base and extracting the neutralized aqueous extract with a second solvent to obtain a purified formula I compound.

15. The process according to claim 14 wherein the impure formula I compound is extracted with a mineral acid solution in the presence of a solvent.

16. The process according to claim 14 wherein the impure formula I compound is extracted with about 2.0 to 6.0 molar equivalents of the mineral acid solution.

17. The process according to claim 16 wherein the mineral acid is selected from the group consisting of sulfuric acid, hydrochloric acid, hydrobromic acid and phosphoric acid, the first solvent and the second solvent are independently selected from the group consisting of toluene, benzene, a xylene, chlorobenzene and a dichlorobenzene and the base is selected from the group consisting of ammonium hydroxide, sodium carbonate and sodium bicarbonate.

18. The process according to claim 17 wherein the mineral acid is sulfuric acid, the first and second solvents are toluene and the base is ammonium hydroxide.

19. The process according to claim IS wherein the 2,3-pyridine or quinolinedicarboxylic acid diester is selected from the group consisting of diethyl 5-ethyl-2,3-pyridinedicarboxylate, diethyl 2,3-pyridinedicarboxylate, diethyl 5-methoxymethyl-2,3-pyridinedicarboxylate, diethyl 2,3-quinolinedicarboxylate and diethyl 5-methyl-2,3-pyridinedicarboxylate.

20. The process according to claim 19 wherein the 2,3-pyridine or quinolinedicarboxylic acid diester is diethyl 5-ethyl-2,3-pyridinedicarboxylate.

* * * * *